United States Patent [19]

Mueller et al.

[11] Patent Number: 4,588,827

[45] Date of Patent: May 13, 1986

[54] PREPARATION OF TETRAHYDROFURAN

[75] Inventors: Herbert Mueller, Frankenthal; Christof Palm, Ludwigshafen, both of Fed. Rep. of Germany

[73] Assignee: BASF Aktiengesellschaft, Ludwigshafen, Fed. Rep. of Germany

[21] Appl. No.: 703,770

[22] Filed: Feb. 21, 1985

[30] Foreign Application Priority Data

Feb. 23, 1984 [DE] Fed. Rep. of Germany ....... 3406471
Sep. 5, 1984 [DE] Fed. Rep. of Germany ....... 3432575

[51] Int. Cl.$^4$ .......................................... C07D 307/08
[52] U.S. Cl. .................................................. 549/509
[58] Field of Search ...................................... 549/509

[56] References Cited

U.S. PATENT DOCUMENTS

| | | | |
|---|---|---|---|
| 2,251,292 | 8/1941 | Reppe | 549/509 |
| 2,251,835 | 8/1941 | Reppe et al. | 549/509 |
| 3,726,905 | 4/1973 | Coates et al. | 549/509 |
| 3,980,672 | 9/1976 | Tomomatsu | 549/429 |
| 4,233,228 | 11/1980 | Mueller et al. | 549/429 |

FOREIGN PATENT DOCUMENTS 850750  9/1952  Fed. Rep. of Germany .
1043342 11/1958  Fed. Rep. of Germany .

OTHER PUBLICATIONS

Reppe et al, Annalen der Chemie, 596, (1955), 81 and 82.

Primary Examiner—Richard L. Raymond
Attorney, Agent, or Firm—John H. Shurtleff

[57] ABSTRACT

Tetrahydrofuran is prepared from a crude alkaline aqueous solution of butane-1,4-diol, as obtained by reaction of acetylene with aqueous formaldehyde and catalytic hydrogenation of the resulting but-2-yne-1,4-diol solution by a process in which the alkaline solution is first neutralized with sulfuric acid and water is then eliminated in the liquid phase at from 200° to 260° C., under superatmospheric pressure and in the presence of phosphoric acid.

8 Claims, No Drawings

PREPARATION OF TETRAHYDROFURAN

The present invention relates to the preparation of tetrahydrofuran by dehydration of butane-1,4-diol using phosphoric acid.

Because of its considerable industrial importance, the dehydration of butane-1,4-diol to tetrahydrofuran has formed the subject of a large number of suggestions for processes. For example, it has been proposed to carry out the dehydration in the liquid phase or over a fixed-bed catalyst in the gas phase, acids, such as sulfuric acid and phosphoric acid, ion exchangers or Lewis acids being recommended as dehydration catalysts (German Pat. Nos. 696,779, 711,709, 850,750 and 1,043,342).

However, these conventional processes have disadvantages, for example that side reactions result in an unacceptable consumption of catalyst, and that in general the yield does not exceed 95%. Ion exchangers have not proven to be sufficiently stable at the required reaction temperatures, and cannot be regenerated to a sufficient extent. If tetrahydrofuran is prepared by the process described in German Pat. No. 1,043,342, where butane-1,4-diol is converted in the presence of from 1 to 5% by weight of sulfuric acid at from 100° to 130° C., the synthesis apparatuses must be lined with particularly resistant material, such as lead, in order to prevent corrosion. Moreover, by-products collect in the sulfuric acid, with the result that the reaction mixture shows a pronounced tendency to foam. In distilling off the tetrahydrofuran formed, it is therefore necessary to dispose of the resulting bottom product prematurely, i.e. before all of the butanediol has been converted to tetrahydrofuran. This gives rise to additional environmental problems. Moreover, the disadvantage of this continuous process is that there is a limit to the number of times sulfuric acid can be reused as a catalyst. Although in theory no catalyst is consumed, resin formation takes place, resulting in frequent shut-downs and hence considerable loss of acid. As much as 10,000 parts of butanediol per part by weight of sulfuric acid are converted by the procedure described in German Pat. No. 1,043,342. Hence, when the process is carried out industrially on a large scale, a considerable amount of sulfuric acid has to be destroyed. The more impure the butanediol used, the more serious is this deficiency. Undistilled butanediol cannot in general be used for the preparation of tetrahydrofuran by this process, since the stated catalyst productivity is ensured only in the case of very pure butanediol.

Butane-1,4-diol is not produced just to be used subsequently in the synthesis of tetrahydrofuran, but is an important intermediate for the production of plastics. The butanediol purification required for this intended use always gives, in addition, a butanediol fraction which is contaminated with by-products and which would be very suitable for the preparation of tetrahydrofuran. In this case, however, it would be necessary to accept a higher sulfuric acid consumption, since these impurities, too, increase in concentration, especially in the acid in the liquid phase. Foaming occurs, and, since the byproducts or polymers formed from these dissovle in the sulfuric acid, the reaction mixture rapidly becomes viscous.

This deficiency is remedied in the process described in German Laid-Open Application DOS No. 2,303,619 by reacting an undistilled crude butanediol with sulfuric acid and with tall oil, and separating off the impurities continuously together with the tall oil. Although this results in an increase in the yield of tetrahydrofuran, tall oil and sulfuric acid are constantly lost.

In the tetrahydrofuran process described in German Pat. No. 711,709, butane-1,4-diol is heated with water to above 250° C. under superatmospheric pressure in the presence of a water-eliminating catalyst. Suitable catalysts of this type are both heterogeneous catalysts and homogeneous ones. Although this process gives relatively high yields, it has not become established in industry because the tetrahydrofuran is contaminated with, in particular, 2,3-dihydrofuran, 3,4-dihydrofuran, carbonyl compounds, and low boilers such as butadiene. The content of dihydrofurans and carbonyl compounds presents serious problems, since these compounds cannot be removed from the tetrahydrofuran by distillation. Further impurities are formed as a result of the tetrahydrofuran produced decomposing into propylene and formaldehyde at the high temperatures.

The requirements which the purity of the tetrahydrofuran has to meet depend on the intended use. Commerical technical-grade tetrahydrofuran is already very pure, its purity usually being greater than 99.8%. However, even a tetrahydrofuran which contains only from 10 to 50 ppm of impurities may be unsuitable for the uses where high requirements have to be met, such as the preparation of polytetrahydrofuran. Tetrahydrofuran having a purity which meets even high requirements cannot be prepared by the process of German Pat. No. 711,709, not even when very expensive distillation is employed. In this case, even the various proposed methods of purification for tetrahydrofuran (U.S. Pat. No. 3,980,672 and European Pat. No. 1,761) do not result in the desired success.

Another reason why the process described in German Pat. No. 711,709 has not become established in industry is that when the process is operated continuously with crude butanediol solutions, as obtained in the hydrogenation of crude butynediol solutions prepared by reacting acetylene with formaldehyde, the tubes become blocked after only a short time owing to resin formation. With increasing time-on-stream, the activity of the reactors decreases, although the feed remains the same. This fall in reactivity can be counteracted by treating the crude solutions beforehand with cation exchangers, as described in Annalen der Chemie, 596 (1955), 81 and 82. In this publication, Reppe et al. have reported that the dehydration of the butanediol to tetrahydrofuran is an equilibrium reaction which is shifted substantially toward the tetrahydrofuran but still permits sufficient butanediol in the product to make this process appear uneconomical. They state in this publication that complete conversion of butane-1,4,-diol to tetrahydrofuran is achieved only when tetrahydrofuran is distilled from the reaction mixture at the rate at which it is formed.

It is an object of the present invention to provide a process for the preparation of tetrahydrofuran which permits crude aqueous solutions of butane-1,4-diol to be converted to tetrahydrofuran having a purity sufficiently high for it to be used for the preparation of polytetrahydrofuran. It is intended, in particular, to achieve conversions to tetrahydrofuran which lie outside the equilibrium concentration described above, i.e. are shifted toward tetrahydrofuran. Furthermore, the process should be capable of being carried out in a manner which is particularly economical and causes little pollution of the environment.

We have found that this object is achieved by a novel process in which tetrahydrofuran is prepared from an aqueous butane-1,4-diol solution by eliminating water in the aqueous phase at elevated temperatures, under superatmospheric pressure and in the presence of an acid, wherein a crude aqueous solution of butane-1,4-diol, obtained by reaction of acetylene with aqueous formaldehyde and catalytic hydrogenation of the resulting but-2-yne-1,4-diol solution, is, when starting with a crude alkaline aqueous solution, neutralized with sulfuric acid, acidified by adding phosphoric acid, and then heated at from 200° to 260° C. under superatmospheric pressure.

The aqueous solutions of butane-1,4-diol which are used as starting solutions in the novel process for the preparation of tetrahydrofuran are obtained in the conventional large-scale industrial conversion of acetylene with aqueous formaldehyde, in which aqueous solutions of but-2-yne-1,4-diol are formed, these solutions being subjected to catalytic hydrogenation (cf. Ullmanns Encyklopmädie der techn. Chemie (1953), volume 3, pages 109–119, and volume 4, pages 754–757, German Published Application DAS No. 2,421,407 and German Laid-Open Application DOS No. 2,536,273.

The aqueous starting solutions are, as a rule, weakly alkaline and have, for example, the following composition: from 20 to 60% by weight of butane-1,4-diol, from 30 to 79% by weight of water, and from 1 to 5% by weight of monoalcohols, such as methanol, propanol and butanol, and unsaturated compounds, such as butenediol. They may furthermore contain small amounts of carbonyl compounds, such as hydroxybutyraldehyde, or the corresponding acetals, polymeric resins and inorganic components, such as sodium salts, dissolved catalyst components and abrasion material from catalysts. Where they contain an alkali, these crude aqueous solutions of butane-1,4-diol are first neutralized with sulfuric acid. The number of equivalents of sulfuric acid used for the neutralization must not be less than the sum of the number of equivalents of base present in the solution. The sum of the number of equivalents of base present can be determined by measuring the base number, for example by titration with N/10 HCL against bromophenol blue. An excess of more than 20 equivalent per cent of sulfuric acid should be avoided.

The starting solution which has been neutralized with sulfuric acid is acidified with phosphoric acid, the aqueous mixture being brought to a pH of, preferably, from 2 to 3 by the addition of the phosphoric acid. The concentration of the phosphoric acid in the butylene glycol starting solution is in general from 0.1 to 0.5% by weight. The mixture is then heated under autogenous pressure at from 200° to 260° C., preferably from 230° to 250° C., the residence time being from 2 to 5 hours. During this procedure, the butanediol is selectively cyclized to tetrahydrofuran, the formation of by-products being avoided. At the same time, from 1 to 2% by weight of the amount of butanediol originally present in the solution remain unconverted in the mixture. This small residual amount of butanediol can be reduced to 0.1–0.3% by weight, for example by cooling the liquid reaction mixture, heated in this manner, to below 100° C. for a mean residence time of not less than 10 minutes, in the absence of a gas phase.

The reaction is advantageously carried out continuously, for example by forcing the crude solution by means of a pump first through a preheater and then through a delay tube in which it is subjected to the stated temperatures. The reaction pressure is chosen to be the same as, or greater than, the vapor pressure of the reaction product at the reaction temperature. Higher pressures can be chosen, but they have no effect on the reaction.

The liquid reaction mixture heated on 200°–260° C. is cooled in, for example, a heat exchanger, advantageously continuously in a tubular heat exchanger. The mean residence time of the reaction mixture in the heat exchanger, in which it is cooled to below 100° C., is, for example, from 10 to 45, preferably from 15 to 30, minutes. After this treatment, which is carried out in the closed system and in the absence of a gas phase, the reaction mixture is passed into a distillation column, advantageously by being let down via a pressure valve, in order to separate off the tetrahydrofuran.

At the bottom of the distillation column, the water initially present in the mixture and that formed during the reaction are run off continuously, while an azeotrope boiling at 65°C. and consisting of about 96% by weight of tetrahydrofuran and 4% by weight of water is obtained at the top of the distillation column. If this mixture is dehydrated, tetrahydrofuran having a purity greater than 99.9% by weight is obtained. The product can be used for the preparation of polytetrahydrofuran without further purification operations.

The process can be carried out batchwise, but the continuous procedure is of course advantageous since in this case the sensible heat of the reacted mixture can most simply be recovered for the isolation of the tetrahydrofuran azeotrope by distillation.

The observed decrease in the residual amount of butanediol on cooling the reaction mixture results in an increase in the content of tetrahydrofuran, so that substantially complete conversion is obtained. This is surprising since such low residual butanediol contents are otherwise achieved only when the starting mixture is subjected to long residence times, e.g. from 6 to 8 hours, when heated at, for example, 250° C. The fact that the advantageous result is obtained with a mean residence time of only 2 hours when the reaction mixture is cooled according to the invention after the heating procedure could not be foreseen, since the reaction rate is generally increased by increasing the temperature. It is also surprising that, for example, a poorer result is obtained if cooling is carried out not to below 100° C. but instead to below 150° C. In this case, only 99.4–99.7% by weight, instead of 99.7–99.9% by weight, of the butanediol is converted to tetrahydrofuran. If cooling is carried out more rapidly than the rate envisaged in the novel process, the good results are again not achieved.

On the basis of the statements by Reppe (Annalen der Chemie, 596 (1955), 81 and 82), the fact that, using the process of the invention, tetrahydrofuran can be prepared from crude aqueous solutions of butane-1,4-diol in 100% yield must be regarded as surprising. Although the process according to the invention is carried out under highly acidic conditions and at elevated temperatures, we have found that, surprisingly, it is also possile to use reaction apparatuses consisting of considerably cheaper materials, such as stainless steel no. 1.4571 and no. 1.4439. It was not to be expected that these materials would prove corrosion-resistant under the process conditions.

EXAMPLE 1

The starting solution used was a crude aqueous 50% strength by weight butane-1,4-diol solution prepared by reaction of acetylene with aqueous formaldehyde (cf. German Published Application DAS No. 2,421,407) and catalytic hydrogenation of the resulting but-2-yne-1,4-diol solution (cf. German Laid-Open Application DOS No. 2,536,273). The base number of the solution was determined as 1.0 mg of KOH/g by titration with N/10 HCL against bromophenol blue as indicator. The solution was brought to pH 7 by admixing 0.1% by weight of sulfuric acid, after which the pH was adjusted to 2.5 by adding 0.15% by weight of phosphoric acid.

The preparation of the tetrahydrofuran from the butanediol solution was carried out in a reaction cascade (of stainless steel 1.4571) which consisted of an electrical preheater and 2 tube reactors connected in series, each having a reaction space of 100 parts by volume. The ratio of the length of the reaction tube to the tube diameter was 70:1.

The acidified butanediol solution was pumped continuously through the electrical preheater, and thus heated to 230° C. It was then fed upward into the tube reactors from below, the said reactors being closed at the exit by means of a pressure-regulating valve which was set at 150 bar. The temperature in the tube reactors during the reaction was from 235° to 245° C., and the mean residence time was 4 hours.

The mixture leaving the reaction vessels was let down in a distillation column, where it was separated into water and a tetrahydrofuran/water azeotrope. The water initially present in the mixture and that formed during the reaction were taken off continuously from the bottom of the distillation column, while a mixture boiling at 66° C. and consisting of tetrahydrofuran and 5.5% by weight of water was obtained via the top of the column. The azeotropic mixture was dehydrated in a conventional manner, for example with the acid of solid dehydrating agents or by extractive distillation. Tetrahydrofuran of very high purity (greater than 99.9% by weight) was obtained. The tetrahydrofuran had a carbonyl number of <0.01 mg of KOH/g and a bromine number of <0.01 g/100 g, was contaminated by <1 ppm of 2,3- and 2,4-dihydrofuran and contained <5 ppm of buta-1,3-diene. The yield was 100% of theory. The tetrahydrofuran obtained could be polymerized by a conventional polymerization method to give polytetrahydrofuran having a color number of <20 APHA. When a very pure industrial tetrahydrofuran which had not been pretreated was used for the same polymerization, the resulting polymers had color numbers of from 50 to 90 APHA.

EXAMPLE 2

(Comparative Example)

Example 1 was repeated, omitting the neutralization with sulfuric acid. Only 70% by weight of the butanediol underwent cyclization to tetrahydrofuran. This unfavorable result could not be improved even by doubling the concentration of phosphoric acid. When an attempt was made to improve the result of this comparative experiment by increasing the temperature to 280° C., substantially greater corrosion of the reaction vessel was observed. The linear corrosion rate, which was <0.015 mm/a for Example 1, was determined as 0.5 mm/a in this case (amount of material removed in mm per annum).

EXAMPLE 3

In the reaction cascade described in Example 1, the acidified butanediol solution described in that example was pumped continuously through the electrical preheater and thus heated to 245° C.

The temperature in the tube reactors during the reaction was from 240° to 255° C., and the mean residence time in the reactor was 2 hours. The liquid reaction mixture leaving the reaction cascade was fed upward through a tubular heat exchanger, where it was cooled to 80° C. during a mean residence time of about 25 minutes, in the absence of a gas phase. The product leaving the condenser was let down continuously into a distillation column through a pressure-regulating valve set at 150 bar. The mixture leaving the column was separated into water and a tetrahydrofuran/water azeotrope. The water initially present in the mixture and that formed during the reaction was taken off continuously from the bottom of the distillation column, while a mixture boiling at 64° C. and essentially consisting of tetrahydrofuran and 5% by weight of water in addition to the monoalcohol impurities initially present in the crude butanediol was obtained via the top of the column. The azeotropic mixture was dehydrated in a conventional manner, for example with the aid of solid dehydrating agents or by extractive distillation. The conventional final distillation of this product gave a tetrahydrofuran of very high purity (greater than 99.9% by weight). The tetrahydrofuran had a carbonyl number of <0.01 mg of KOH/g and a bromine number of <0.01 g/100 g, was contaminated by <1 ppm of 2,3- and 2,4-dihydrofuran, and contained <5 ppm of buta-1,3-diene. The selectivity was 100% of theory, and the yield 99.8%. The tetrahydrofuran obtained could be polymerized by a conventional polymerization method to give polytetrahydrofuran having a color number of <20 APHA. When a very pure industrial tetrahydrofuran which had not been pretreated was used for the same polymerization, the resulting polymers had color numbers of from 50 to 90 APHA.

EXAMPLE 4

(Comparative Example)

Example 2 was repeated, omitting the neutralization wih sulfuric acid, and cooling the reaction mixture to 40° C. in the course of from 1 to 5 minutes by intensive cooling. In this procedure, only 99% by weight of the butanediol underwent cyclization to tetrahydrofuran. This unfavorable result could not be improved even by doubling the concentration of phosphoric acid. When an attempt was made to improve the result of this comparative experiment by increasing the temperature to 280° C., substantially greater corrosion of the reaction vessel was observed. The linear corrosion rate, which was >0.015 mm/a for Example 3, was determined as 0.5 mm/a in this case (amount of material removed in mm per annum).

We claim:

1. A process for the preparation of tetrahydrofuran from an aqueous solution of butane-1,4-diol by eliminating water in the liquid phase at elevated temperatures, under superatmospheric pressure and in the presence of an acid, wherein a crude alkaline aqueous solution of butane-1,4-diol, obtained by reaction of acetylene with aqueous formaldehyde and catalytic hydrogenation of the resulting but-2-yne-1,4-diol solution, is, neutralized with sulfuric acid, and is then acidified by adding phosphoric acid and heated at from 200° to 260° C. under superatmospheric pressure.

2. A process as claimed in claim 1, wherein the elimination of water is carried out at from 230° to 245° C.

3. A process as claimed in claim 1, wherein the pH is brought to 2-3 by adding phosphoric acid.

4. A process as claimed in claim 1, wherein the liquid reaction mixture which has been heated at 200°-260° C. is cooled to below 100° C. during a mean residence time of not less than 10 minutes and in the absence of a gas phase.

5. A process as claimed in claim 1, wherein the liquid reaction mixture is cooled to below 100° C. during a mean residence time of from 15 to 30 minutes.

6. A process as claimed in claim 1 wherein the amount of sulfuric acid used for neutralizing the crude aqueous solution is not more than 20 equivalent per cent excess with reference to the equivalents of base present in the solution.

7. A process as claimed in claim 6 wherein the solution neutralized with sulfuric acid is then brought to a pH of 2-3 by adding phosphoric acid and water is eliminated in the presence of said phosphoric acid at from 230° to 245° C.

8. A process as claimed in claim 7 wherein the liquid reaction mixture which has been heated at 230° to 245° C. is cooled to below 100° C. during a mean residence time of not less than 10 minutes.

* * * * *